(12) United States Patent
Daimer et al.

(10) Patent No.: US 11,932,573 B2
(45) Date of Patent: Mar. 19, 2024

(54) ELEMENT COMPOSED OF GLASS DISPLAYING REDUCED ELECTROSTATIC CHARGING

(71) Applicant: SCHOTT AG, Mainz (DE)

(72) Inventors: Johann Daimer, Oberahrain (DE); Martin Zöttl, Tiefenbach (DE)

(73) Assignee: SCHOTT AG, Mainz (DE)

( * ) Notice: Subject to any disclaimer, the term of this patent is extended or adjusted under 35 U.S.C. 154(b) by 995 days.

(21) Appl. No.: 16/737,185

(22) Filed: Jan. 8, 2020

(65) Prior Publication Data

US 2020/0216352 A1  Jul. 9, 2020

(30) Foreign Application Priority Data

Jan. 8, 2019 (DE) ................ 10 2019 100 261.3

(51) Int. Cl.
| | | |
|---|---|---|
| *C03C 3/091* | (2006.01) | |
| *A61B 90/98* | (2016.01) | |
| *A61L 31/02* | (2006.01) | |
| *C03C 3/076* | (2006.01) | |
| *C03C 3/083* | (2006.01) | |
| *C03C 3/089* | (2006.01) | |
| *C03C 4/00* | (2006.01) | |
| *C03C 15/00* | (2006.01) | |
| *C03C 21/00* | (2006.01) | |
| *C03C 23/00* | (2006.01) | |
| *G06K 19/07* | (2006.01) | |
| *H01H 36/00* | (2006.01) | |

(52) U.S. Cl.
CPC .............. *C03C 3/091* (2013.01); *A61B 90/98* (2016.02); *A61L 31/026* (2013.01); *C03C 3/076* (2013.01); *C03C 3/083* (2013.01); *C03C 3/089* (2013.01); *C03C 4/0007* (2013.01); *C03C 15/00* (2013.01); *C03C 21/002* (2013.01); *C03C 23/007* (2013.01); *C03C 23/008* (2013.01); *G06K 19/0723* (2013.01); *C03C 2204/00* (2013.01); *H01H 36/00* (2013.01); *H01H 2239/008* (2013.01)

(58) Field of Classification Search
CPC ......... C03C 3/091; C03C 3/083; C03C 3/085; C03C 3/087; C03C 3/112; C03C 4/0007; C03C 15/00; C03C 21/00; C03C 21/001; C03C 21/002
See application file for complete search history.

(56) References Cited

U.S. PATENT DOCUMENTS

| | | | |
|---|---|---|---|
| 3,949,335 | A | 4/1976 | Morgan |
| 4,315,054 | A | 2/1982 | Werner |
| 5,121,748 | A | 6/1992 | Ditz |
| 2006/0077561 | A1 | 4/2006 | Yamada |
| 2013/0287977 | A1 | 10/2013 | Mashima |
| 2014/0144492 | A1 | 5/2014 | Sakamoto |
| 2017/0166473 | A1 | 6/2017 | Miyasaka |
| 2020/0039877 | A1* | 2/2020 | Guo ............ C03C 21/006 |

FOREIGN PATENT DOCUMENTS

| | | | |
|---|---|---|---|
| CN | 103228586 | 7/2013 | |
| DE | 2930912 | 7/1979 | |
| DE | 4015264 | 7/1991 | |
| JP | S5795023 | 6/1982 | |
| JP | H07225202 | 8/1995 | |
| JP | H11171599 | 6/1999 | |
| JP | 2006113142 | 4/2006 | |
| WO | 2007139069 | 6/2007 | |
| WO | WO-2007139069 A1 * | 12/2007 | ........ C03C 21/002 |
| WO | 2016199618 | 12/2016 | |
| WO | 2017010356 | 1/2017 | |
| WO | 2018164904 | 9/2018 | |

\* cited by examiner

*Primary Examiner* — Elizabeth A. Bolden
(74) *Attorney, Agent, or Firm* — Ruggiero McAllister & McMahon LLC

(57) ABSTRACT

An element composed of glass displaying reduced electrostatic charging is provided. The element is suitable as a housing component for electronic elements, an element implantable in the human or animal body including glass tubes for reed switches or transponders and/or implants. The glass includes at least one alkali metal and/or an alkali metal oxide and has a surface. The concentration of at least one alkali metal and/or the alkali metal oxide increases from the surface in a direction of an interior of the element in such a way that a maximum concentration of the alkali metal and/or the alkali metal oxide occurs at a distance of not more than 60 nanometres, measured perpendicularly from the surface.

22 Claims, 12 Drawing Sheets

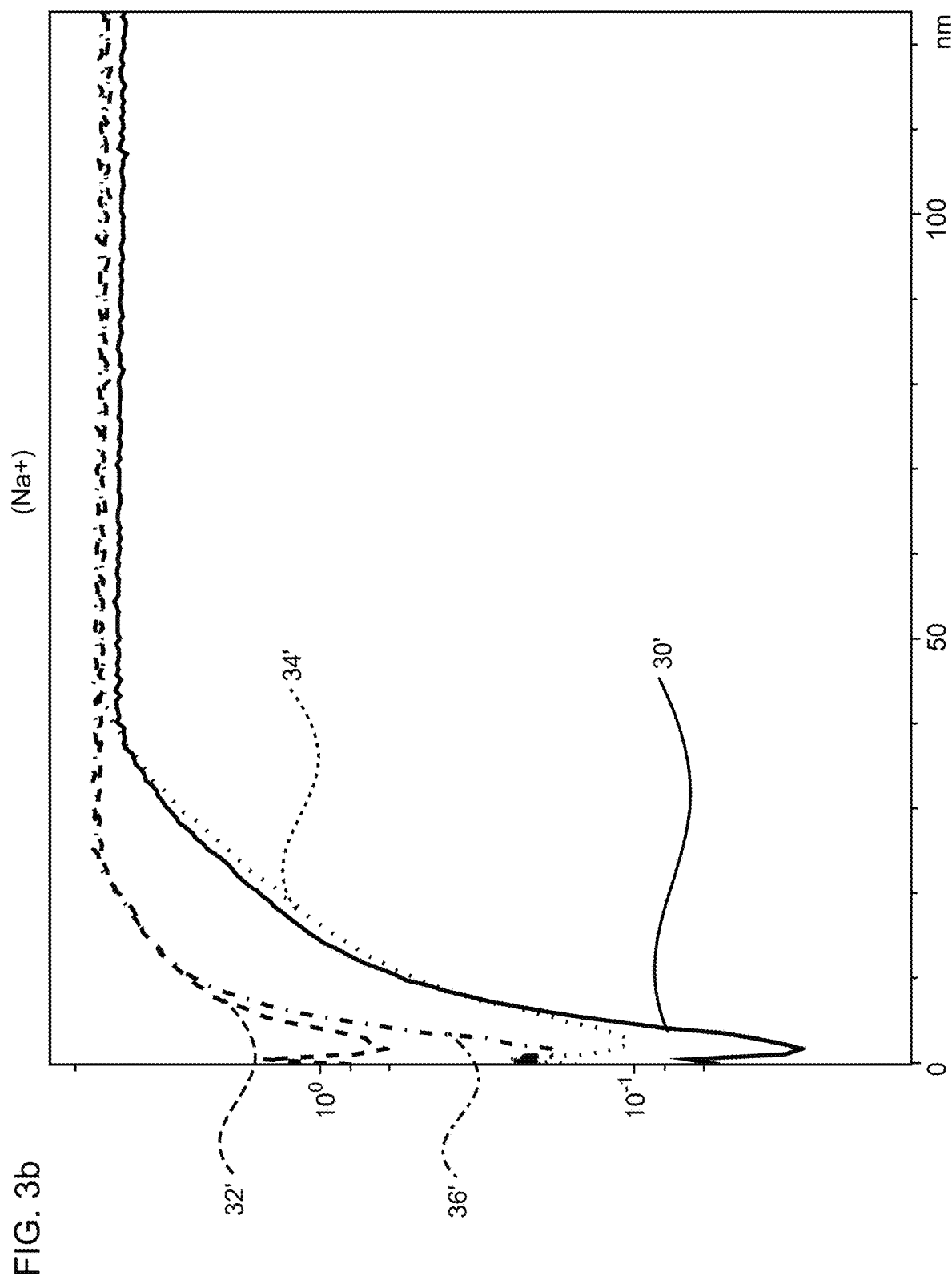

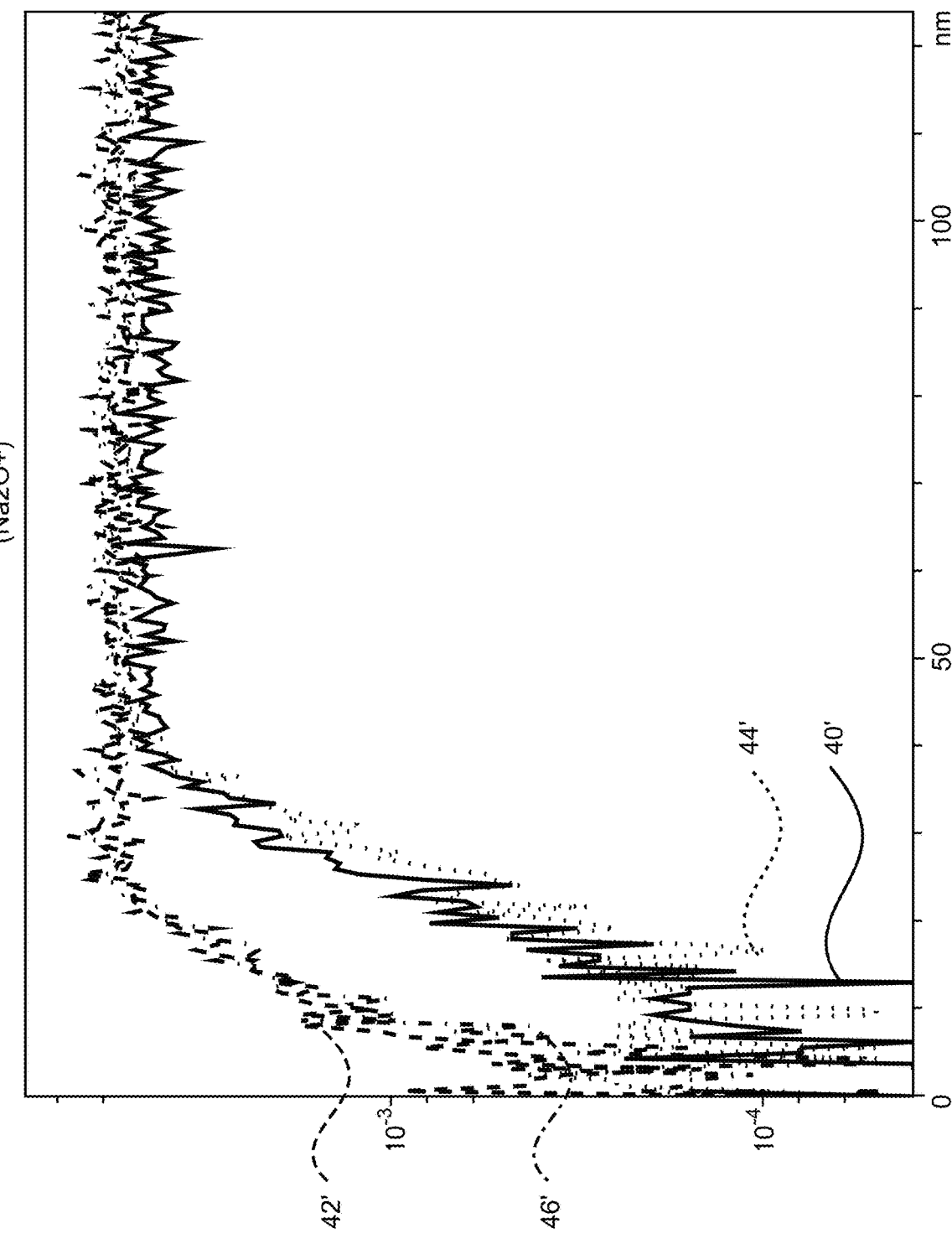

ELEMENT COMPOSED OF GLASS DISPLAYING REDUCED ELECTROSTATIC CHARGING

CROSS REFERENCE TO RELATED APPLICATIONS

This application claims benefit under 35 USC § 119 of German Application 10 2019 100 261.3 filed Jan. 8, 2019, the entire contents of which are incorporated herein by reference.

BACKGROUND

1. Field of the Invention

The invention relates to an element composed of glass which comprises at least one alkali metal and/or an alkali metal oxide, and also a housing component for the housing of electronic elements and/or elements which are implantable in the human or animal body, referred to as implants for short, which comprises at least the element composed of glass.

2. Description of Related Art

Elements composed of glass can, due to their high electrical resistance, accumulate charge carriers, in particular at their surface, during processing thereof and as a result have electrostatic potentials which are also referred to as electrostatic charging.

If such electrostatically charged elements are used for electrical applications, electric or electronic switching processes can be prevented thereby or even be independently triggered thereby. During processing and working of electrostatically charged elements composed of glass, too, malfunctions can be triggered thereby, especially when these elements come into contact with further electrical assemblies or are constructed using these corresponding switching arrangements.

Elements composed of glass which are configured as glass tubes are used, in particular, for the production of reed switches or RFID transponders. In the case of reed switches, ferromagnetic contact tabs are typically fused into a glass tube in such a way that they overlap the glass tube in the longitudinal direction while in the transverse direction they are generally at only a small distance from one another. When a magnetic field acts from outside the glass tube, the switch tabs come into contact and close the switch. Reed switches can be used under virtually all environmental conditions since the contact tabs are hermetically sealed inside the glass tubes and are thus protected against, for instance, dirt or wetness. In the case of RFID transponders, too, it is necessary for many applications to achieve hermetic encapsulation, especially when the transponders are implanted in living beings. For these applications too, glass elements which can be configured as glass tubes are frequently used.

In the production of glass tubes for such or similar purposes, a starting tube which has the desired internal and external diameters and has been, inter alia, drawn directly from the melt is often cut into glass tube sections having the desired length. The parting into shorter sections can, for example, be carried out by scoring and breaking. Glass elements brought to the desired length can, depending on the application, be worked and processed further in many ways before they are hermetically sealed. Thus, the quality of the cut edges is often improved by fire polishing.

US 2013/0287977 A1 describes a glass tube for reed switches which makes it possible to prevent possible splintering and cracking of its end parts by forming a compressive stress layer having a length from one end face in a range from 0.1 to 0.6 millimetres on an exterior circumferential surface of the end part.

Glass elements are, as described, usually produced by hot shaping processes and optionally cleaned. Due to the production processes for the glass elements, especially as a result of hot shaping, components can become depleted in the region of the surface of the glass elements. In general, when the electrical conductivity of the glass element is reduced, for example in the region of the surface, greater electrostatic charging of the glass element can occur. If the glass element is processed on an industrial scale, especially in mass production, excessive electrostatic charges can lead to malfunctions in the production process. In particular, the individual elements can adhere to one another and/or to machine components, in particular transport devices, and thus block and/or at least interfere with the courses of the process.

Excessive electrostatic chargeability of the glass is also disadvantageous in use as, in particular, reed glass or transponder glass since it can lead to electrical and/or magnetic influences on the function of the reed switch or RFID transponder. In addition, the tubular glass elements can attract undesirable particles such as dust. If such components are installed in electronic appliances, damage to the appliances can occur as a result of excessive electrostatic discharges.

On the other hand, a certain electrostatic chargeability can assist further processing of the glass elements, for example when they adhere better to transport devices and less readily slip due to, for example, vibrations or shocks.

SUMMARY

In the light of this background, it is an object of the invention to provide elements composed of glass and housing components at least comprising such elements composed of glass, in the case of which the chargeability is optimized. In particular, this means that the electrostatic chargeability is balanced between the avoidance of excessive electrical chargeability and no electrostatic chargeability.

The invention provides an element composed of glass which comprises at least one alkali metal and/or an alkali metal oxide. Alkali metals and alkali metal oxides are also used as constituents of a glass in order to reduce the viscosity of the glass and assist melting of the glass and/or subsequent hot shaping.

When the elements according to the invention composed of glass have a reduced electrostatic chargeability, they can also, as indicated above, hereby advantageously have decreased attraction for particles, which can increase the yield in further processing thereof and decrease consequent malfunctions in electrical arrangements.

The element of the invention composed of glass has at least one surface and the concentration of at least one alkali metal and/or the alkali metal oxide increases from the surface in the direction of the interior of the element composed of glass. The concentration of this alkali metal and/or the alkali metal oxide accordingly has a minimum value at or near the surface. The concentration increases with increasing distance from the surface in the direction of the interior of the element composed of glass. As a result, the concentration of this alkali metal and/or the alkali metal oxide is lower at the surface of the element composed of glass than in the direction of the interior thereof, so that it in principle has an electrostatic chargeability.

According to the invention, the concentration of the at least one alkali metal and/or the alkali metal oxide increases in the direction of the interior of the element composed of glass in such a way that the maximum concentration of at least one alkali metal and/or the alkali metal oxide in the element composed of glass occurs at a distance of not more than 60 nanometres, advantageously not more than 50 nanometres, more advantageously not more than 40 nanometres, even more advantageously not more than 30 nanometres and especially advantageously not more than 20 nanometres, measured perpendicularly to the surface.

It has been found that elements composed of glass which have an abovementioned concentration profile of an alkali metal and/or the alkali metal oxide become electrostatically charged only to a reduced extent which is, for example, suitable in further processing. As a result of the maximum concentration of the alkali metal and/or the alkali metal oxide being reached within a distance of not more than 60 nanometres, advantageously not more than 50 nanometres, more advantageously not more than 40 nanometres, even more advantageously not more than 30 nanometres and especially advantageously not more than 20 nanometres, from the surface, a reduction in the electrostatic chargeability can be achieved in an advantageous way.

In one embodiment of the invention, the concentration of the at least one alkali metal and/or the alkali metal oxide at the surface of the element is at least 2 percent, in particular at least 4 percent, preferably at least 6 percent, more preferably at least 8 percent, even more preferably at least 10 percent and optionally particularly preferably at least 15 percent, optionally even more preferably at least 60 percent, of the abovementioned maximum concentration of the at least one alkali metal and/or the alkali metal oxide in the element composed of glass.

Samples of glass elements having the abovementioned minimum concentrations of the alkali metal and/or the alkali metal oxide at or near the surface display increased surface conductivity when compared to different concentration profiles.

The mean of the abovementioned maximum concentration of the at least one alkali metal and/or alkali metal oxide and the concentration of the at least one alkali metal and/or the alkali metal oxide at the surface preferably occurs at a distance of at least 1 nanometre, preferably at least 5 nanometres, and not more than 50 nanometres, preferably not more than 25 nanometres, measured perpendicularly from the surface.

In this way, a largely continuous increase, at least in the region close to the surface, in the concentration in the direction of the interior of the element composed of glass can typically be defined.

In one embodiment of the invention, the concentration of the at least one alkali metal and/or the alkali metal oxide at the surface of the element is not more than 60 percent, preferably not more than 75 percent, particularly preferably not more than 90 percent, more preferably not more than 95 percent and especially preferably not more than 99 percent, of the abovementioned maximum concentration of the at least one alkali metal and/or the alkali metal oxide in the element composed of glass.

The value at the surface can, apart from its actual meaning, also have the meaning of the mean over a depth range of from 0 to 5 nanometres or else have the meaning of the minimum value in the depth range of from 0 to 5 nanometres. This applies generally when the value at the surface is being spoken of.

Samples of glass elements having the abovementioned maximum concentrations of the alkali metal and/or the alkali metal oxide at or close to the surface no longer display any significant increase in the surface conductivity on comparison of different concentration profiles.

Rather, abovementioned maximum concentrations have the advantage that elements composed of glass, for example glass tubes, have a suitable electrostatic chargeability, i.e. an electrostatic chargeability which is present but is not too high and is therefore optimized, during further processing thereof.

In an embodiment of the invention, the glass comprises at least a proportion of alkalis of at least 18 percent by weight, advantageously at least 16 percent by weight, likewise advantageously at least 15 percent by weight, likewise advantageously at least 12 percent by weight, likewise advantageously at least 10 percent by weight, particularly advantageously at least 8 percent by weight.

A particularly suitable alkali metal oxide is sodium oxide ($Na_2O$). Sodium oxide is typically used so that glass melts more easily. The glass advantageously comprises at least 15 percent by weight of $Na_2O$, advantageously at least 13 percent by weight, likewise advantageously at least 10 percent by weight, likewise advantageously at least 8 percent by weight, likewise advantageously at least 4 percent by weight, particularly advantageously at least 2 percent by weight.

Further particularly suitable alkali metals are $K_2O$ and/or $Li_2O$. The glass advantageously comprises at least 10 percent by weight of $K_2O$, advantageously at least 8 percent by weight, likewise advantageously at least 6 percent by weight, likewise advantageously at least 5 percent by weight, likewise advantageously at least 0.7 percent by weight.

The glass can likewise advantageously contain $Li_2O$ as compulsory component.

The alkali metal oxides mentioned can, in particular, also be used in any combination with one another. Analogously, the abovementioned minimum contents apply in any desired combination.

The electrostatic properties of the glass element can be influenced by this combination. In particular, the total concentration of alkali metal oxides is advantageously not more than 20 percent by weight, likewise advantageously not more than 17 percent by weight, likewise advantageously not more than 13 percent by weight.

The concentration of the sodium oxide can increase from a minimum value at or close to the at least one surface in the direction of the interior of the element. Furthermore, the concentration of the sodium oxide has an essentially constant plateau value in the interior of the element beyond a distance of not more than 50 nanometres, advantageously not more than 30 nanometres, more advantageously not more than 25 nanometres, from the at least one surface.

In particular, the minimum value of the concentration of the sodium oxide is at least 1 percent, preferably at least 2 percent, particularly preferably at least 5 percent, of the plateau value.

These minimum values of the concentration of the sodium oxide have been found to be a good compromise for optimized electrostatic chargeability.

However, it can optionally also be provided for the minimum value of the concentration of the sodium oxide to be at least 7.5 percent, preferably at least 10 percent, particularly preferably at least 15 percent and even more preferably at least 20 percent, of the plateau value.

The concentration of the lithium oxide can increase from a minimum value at or close to the at least one surface in the direction of the interior of the element. Furthermore, the concentration of the lithium oxide has an essentially constant plateau value in the interior of the element beyond a distance of not more than 50 nanometres, advantageously not more than 30 nanometres, from the at least one surface.

In particular, the minimum value of the concentration of the lithium oxide is also at least 1.5 percent, preferably at least 3 percent, particularly preferably at least 5 percent, of the plateau value.

These minimum values of the concentration of the lithium oxide have likewise been found to be a good compromise for optimized electrostatic chargeability.

The concentration of the potassium oxide can increase from a minimum value at or close to the at least one surface in the direction of the interior of the element. Furthermore, the concentration of the potassium oxide has an essentially constant plateau value in the interior of the element beyond a distance of not more than 30 nanometres, preferably not more than 50 nanometres, from the at least one surface.

In particular, the minimum value of the concentration of the potassium oxide is also at least 1 percent, preferably at least 2 percent, particularly preferably at least 5 percent, of the plateau value.

These minimum values of the concentration of the potassium oxide have likewise been found to be a good compromise for optimized electrostatic chargeability.

The glass preferably comprises, measured at a distance of at least 50 nanometres measured perpendicularly from the surface, the following proportions in percent by weight on an oxide basis:
   silicon dioxide ($SiO_2$): from 50 to 77 percent,
   aluminium oxide ($Al_2O_3$): from 0 to 10 percent, in particular 0.5-7 percent,
   in particular 1-7 percent,
   boron trioxide ($B_2O_3$): from 0 to 10 percent,
   iron(III) oxide ($Fe_2O_3$): from 0 to 10 percent,
   sodium oxide ($Na_2O$): from 0 to 18 percent, in particular 1-15 percent,
   potassium oxide ($K_2O$): from 0 to 17 percent,
   lithium oxide ($Li_2O$): from 0 to 6 percent, in particular 0-5 percent,
   total oxides of Ca, Mg, Ba, Sr and/or Zn: from 1 to 15 percent.

A composition having the proportions mentioned with fluorine (F) additionally being present in a proportion of from 0 to 4 percent (percent by weight), preferably from 0 to 3.5 percent (percent by weight), is also possible.

A composition having the proportions mentioned with the total of $Na_2O$, $Li_2O$ and $K_2O$ additionally being from 8 to 24 percent (percent by weight) is also possible.

A composition having the proportions mentioned with $TiO_2$ additionally being present in an amount of 0-1 percent (percent by weight) is also possible. Furthermore, $Sb_2O_3$ can be present, especially in the customary amounts for refining agents.

In a preferred variant, the following proportions in percent by weight can also be present:
   silicon dioxide ($SiO_2$): from 50 to 77 percent,
   aluminium oxide ($Al_2O_3$): from 0.5 to 7 percent,
   boron trioxide ($B_2O_3$): from 0.1 to 8 percent,
   iron(III) oxide ($Fe_2O_3$): from 0 to 8 percent,
   sodium oxide ($Na_2O$): from 0 to 18 percent,
   potassium oxide ($K_2O$): from 0 to 17 percent,
   lithium oxide ($Li_2O$): from 0 to 6 percent,
   total oxides of Ca, Mg,
   Ba and Sr: 0-15 percent.

A composition having the proportions mentioned with fluorine (F) additionally being present in a proportion of from 0 to 4 percent (percent by weight) is also possible.

A composition having the proportions mentioned with the total of $Na_2O$, $Li_2O$ and $K_2O$ additionally being from 8 to 24 percent (percent by weight) is also possible.

A composition having the proportions mentioned with $TiO_2$ being additionally present in an amount of 0-1 percent (percent by weight) is also possible. Furthermore, $Sb_2O_3$ can be present, especially in the customary amounts for refining agents.

In a further preferred variant, the following proportions in percent by weight can also be present:
   silicon dioxide ($SiO_2$): from 50 to 77 percent,
   aluminium oxide ($Al_2O_3$): from 0.5 to 7 percent,
   boron trioxide ($B_2O_3$): from 0.1 to 8 percent,
   iron(III) oxide ($Fe_2O_3$): from 0 to 8 percent,
   sodium oxide ($Na_2O$): from 0 to 18 percent,
   potassium oxide ($K_2O$): from 0 to 17 percent,
   lithium oxide ($Li_2O$): from 0 to 6 percent,
   total oxides of Ca, Mg, Ba, Sr and Zn: from 3.5-17 percent.

A composition having the proportions mentioned with fluorine (F) also being present in a proportion of from 0 to 4 percent (percent by weight) is also possible.

A composition having the proportions mentioned with the total of $Na_2O$, $Li_2O$ and $K_2O$ additionally being from 8 to 24 percent (percent by weight) is also possible.

A composition having the proportions mentioned with $TiO_2$ additionally being present in an amount of 0-1 percent (percent by weight) is also possible. Furthermore, $Sb_2O_3$ can be present, especially in the customary amounts for refining agents.

A ratio of $Na_2O/K_2O$ of >0.1; preferably $Na_2O/K_2O$ of >0.3; more preferably $Na_2O/K_2O$ of >1 can be provided; particularly preferably is the ratio of $Na_2O/K_2O$ of >1.4.

A minimum proportion of $Fe_2O_3$ of 1 percent by weight can be advantageous, especially when the material is to be able to be fused by means of infrared radiation.

As indicated above, the electrostatic chargeability can be related to the electrical conductivity of a glass element. For example, it was able to be shown that at the abovementioned surface conductivity, the electrostatic chargeability can be reduced to such an extent that, in particular, adhesion of particles to the glass elements and/or adhesion of the glass elements to one another can be largely avoided.

Furthermore, the invention provides a glass tube for reed switches or transponders which is formed by an abovementioned element composed of glass or at least comprises such an element. Glass elements configured in this way as glass tubes are particularly advantageous for the production of reed switches or RFID transponders.

The glass tube is preferably configured as cylindrical tube having an exterior surface and an interior surface and a uniform wall thickness.

The glass tube preferably has an external diameter of less than 6 millimetres, preferably less than 3 millimetres, particularly preferably less than 2.5 millimetres.

Furthermore, the glass tube preferably has a ratio of wall thickness to external diameter of less than ⅓, preferably less than ⅕.

The ratio of length to external diameter of the glass tube is preferably less than 20, preferably less than 10, advantageously less than 5.

Furthermore, the invention provides a reed switch or transponder which comprises an abovementioned glass tube, with the glass tube forming, in particular, the housing.

BRIEF DESCRIPTION OF THE DRAWINGS

FIGS. 3a and 3b are depth profiles of sodium ions generated by means of ToF-SIMS on four glass reed tubes;
FIGS. 4a and 4b are depth profiles of silicon ions generated by means of ToF-SIMS on four glass reed tubes.

DETAILED DESCRIPTION

Figure 1A:
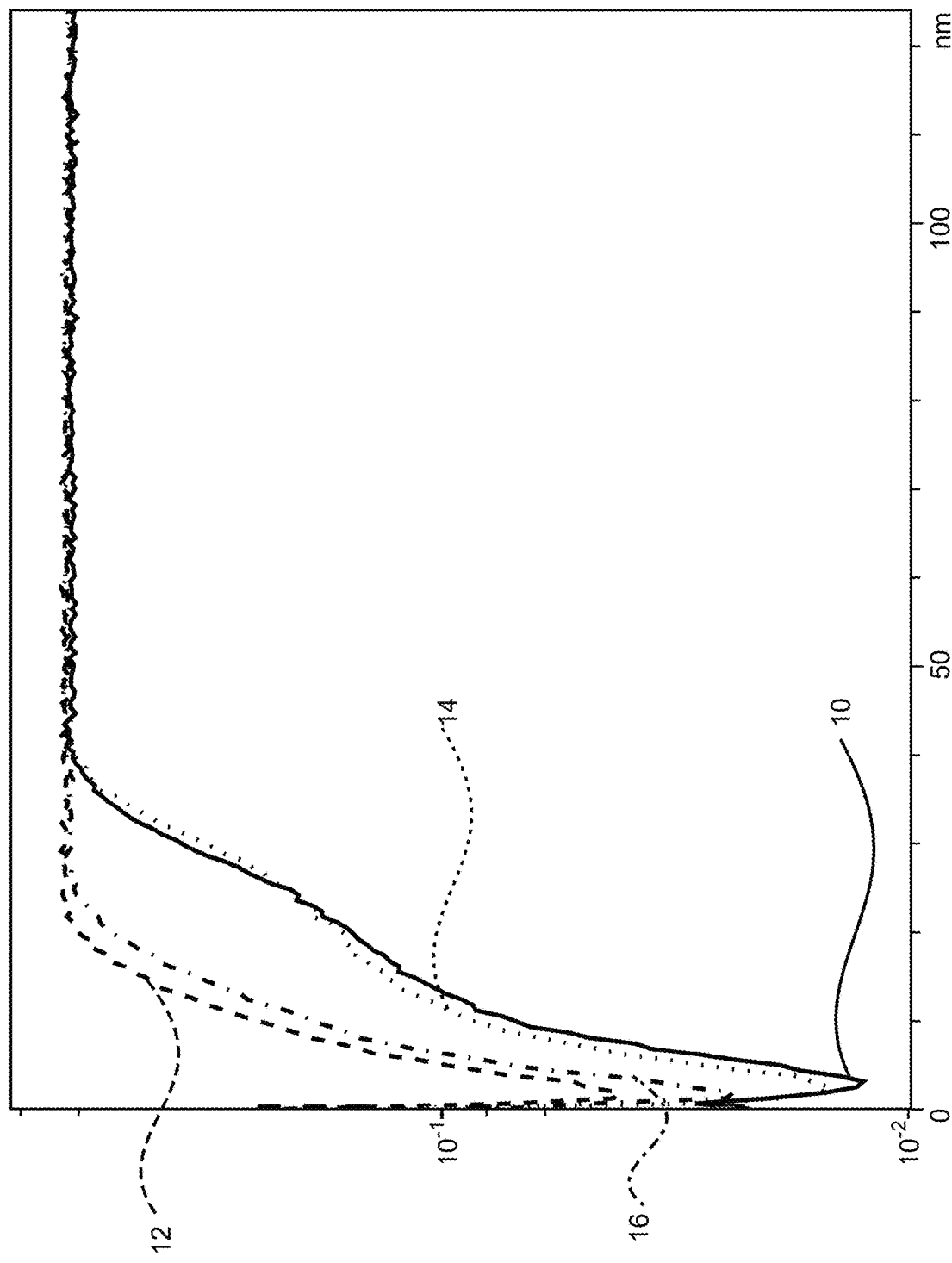
FIGS. 1a and 1b are depth profiles of lithium ions generated by means of ToF-SIMS on four glass reed tubes.

The measured depth profiles of various glass components shown in FIGS. 1a to 5b and FIG. 6 were determined on the exterior surfaces of four different glass reed tubes by means of time-of-flight secondary ion mass spectrometry (ToF-SIMS). The four glass tubes of FIG. 1a are of the same type here as the four glass tubes of FIG. 1b. The same applies to the glass tubes of FIGS. 2a and 2b, 3a and 3b, 4a and 4b, and also 5a and 5b.

In this ToF-SIMS method, a surface is bombarded with a high-energy primary ion beam, resulting in neutral particles, electrons and secondary ions being emitted from the surface. The secondary ions are separated as a function of their masses in a time-of-flight mass spectrometer (ToF spectrometer) and their relative number to one another is detected. This relative number is a measure of the concentration of the respective secondary ion as a function of the glass depth.

Figure 1B:
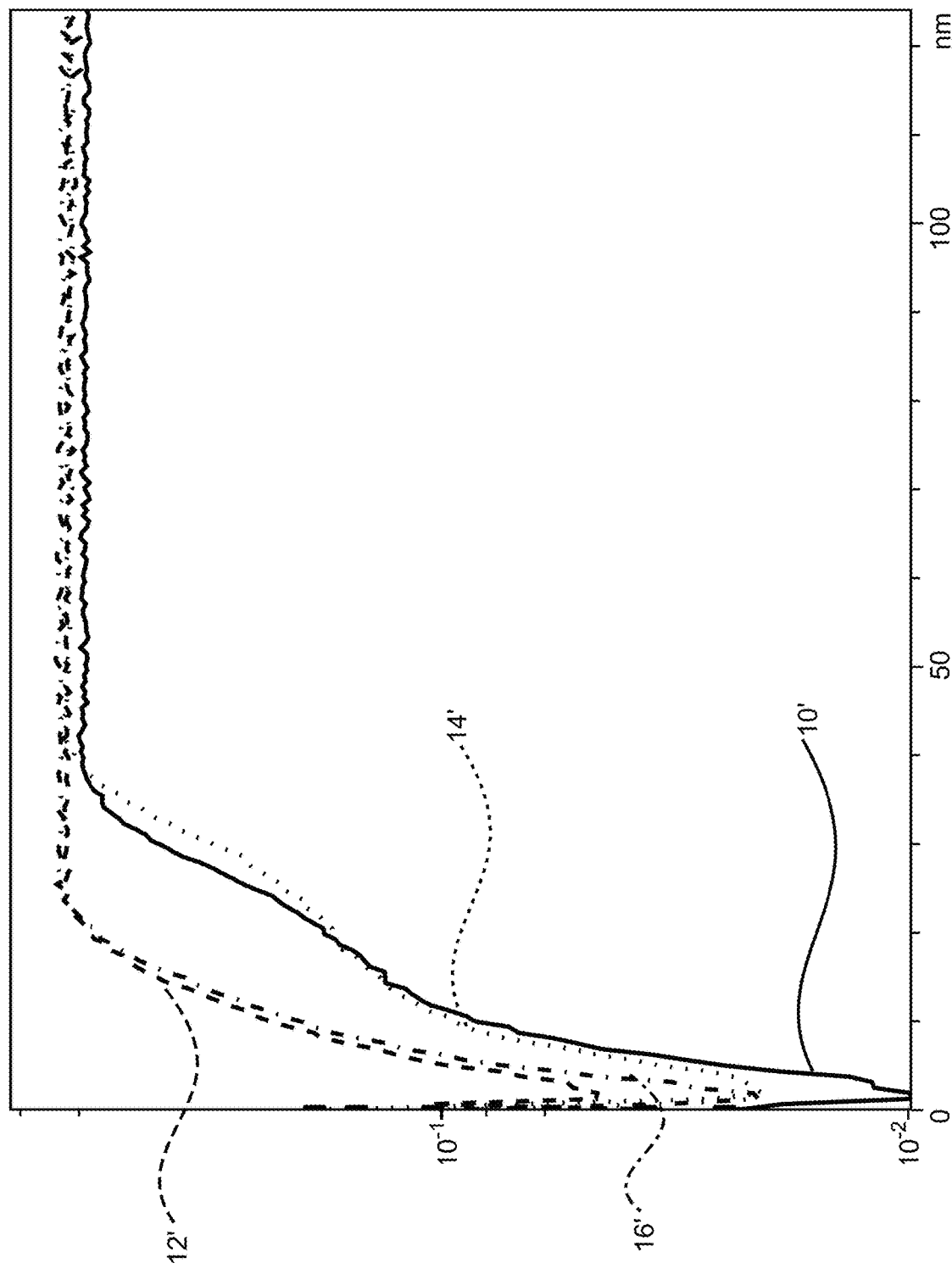

In FIGS. 1a and 1b, the concentration of lithium ions determined in this way is shown in the direction of the y axis. The concentration is plotted as a function of the depth in the direction of the x axis, that is to say as a function of the distance from the exterior surface of the glass element in the direction of the interior of the glass element. For this purpose, the rate of removal of material from the surface produced by the primary ion beam was determined and the depth in nanometres was thus calculated from the radiation time. The indications of x axis and y axis relate to a conventional two-dimensional Cartesian coordinate system in which the x axis runs horizontally and the y axis runs vertically, with the two axes intersecting at their respective zero value.

The four measured concentration profiles of lithium ions as a function of the depth 10, 12, 14 and 16 (FIG. 1a) were determined on four different glass reed tubes each having a diameter of 2.06 millimetres. The same applies to the profiles 10', 12', 14', 16' (FIG. 1b) on the same type of glass tubes in each case.

It should be noted that no absolute concentrations are determined by means of the ToF-SIMS method. To allow better comparability, the profiles were normalised to the intensity of silicon at the end of the measurement. The concentrations are accordingly plotted in arbitrary units (y axis). The concentration profiles 10, 12, 14 and 16 (and also 10', 12', 14' and 16') along in each case the y axis are thus relative values.

The measured concentration profiles of the lithium ions as a function of the depth 10, 12, 14 and 16 (and also 10', 12', 14' and 16') represent merely approximations of the concentration profiles actually present in the material because of the ToF-SIMS method. In particular, the fluctuations in the concentration profiles depicted are normal inaccuracies of such measurement methods.

In FIGS. 1a and 1b, the concentration determined in this way is shown as a function of the glass depth. Here, 10, 12, 14 and 16 (and also 10', 12', 14' and 16') were determined as a function of the depth on four different glass reed tubes each having a diameter of 2.06 millimetres.

The concentration profiles 10, 20, 30 and 40 are for the same sample. Likewise, the concentration profiles 12, 22, 32 and 42 can be assigned to one sample and the concentration profiles 14, 24, 34 and 44 to a further sample. An analogous situation also applies to the concentration profiles 16, 26, 36 and 46. A corresponding situation also applies to the concentration profiles 10', 20', 30' and 40', etc.

The lithium oxide concentration profile 10 measured on a first glass tube assumes a minimum value in the region close to the surface. The value increases in the direction of the interior of the glass tube. Beyond a distance of about 45 nanometres from the surface in the interior of the element, an essentially constant plateau value is attained. Here, the minimum value is about 2 percent of the plateau value.

The lithium oxide concentration profile 12 measured on a second glass tube displays a significantly different behaviour. A minimum value is attained at or close to the surface, and beyond a depth of only about 25 nanometres a plateau value, which represents the maximum value, is attained. Here, the minimum value is about 6 percent of the plateau value.

The lithium oxide concentration profile 14 measured on a third glass tube once again shows a behaviour similar to the profile 10. A minimum value is attained at or close to the surface. Beyond a depth of about 45 nanometres, a plateau value, which represents the maximum value, is attained. Here, the minimum value is about 2 percent of the plateau value.

A behaviour similar to the second glass tube is also observed for the concentration profile 16 of the fourth glass. Here too, the lithium ion concentration firstly decreases sharply at or close to the surface and then attains a plateau value at a depth of only about 25 nanometres. Here, the minimum value is about 3.5 percent of the plateau value.

The profiles shown in FIG. 1b correspond essentially to those of FIG. 1a.

Figure 2A:
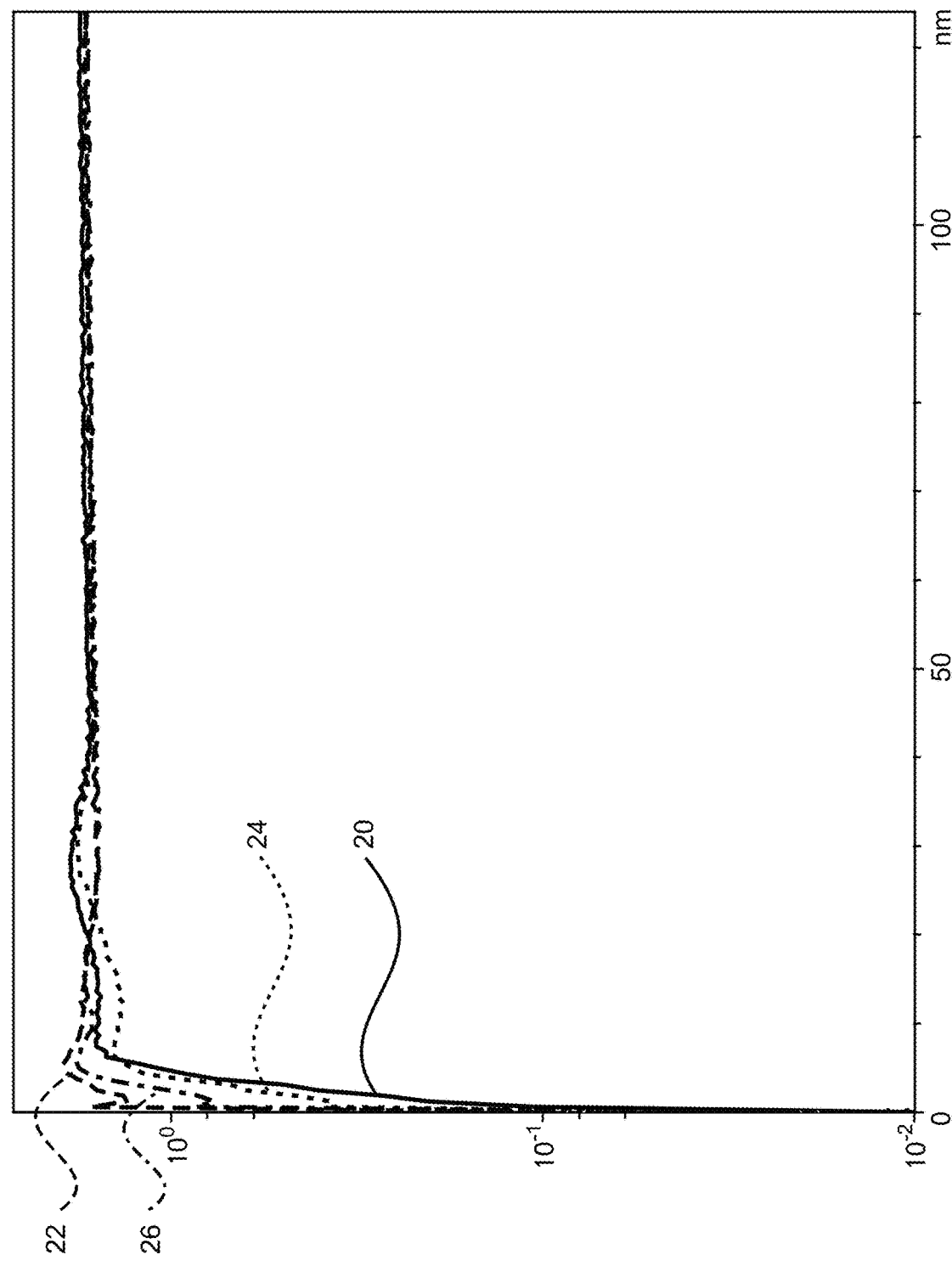
FIGS. 2a and 2b are depth profiles of potassium ions generated by means of ToF-SIMS on four glass reed tubes.
Figure 2B:
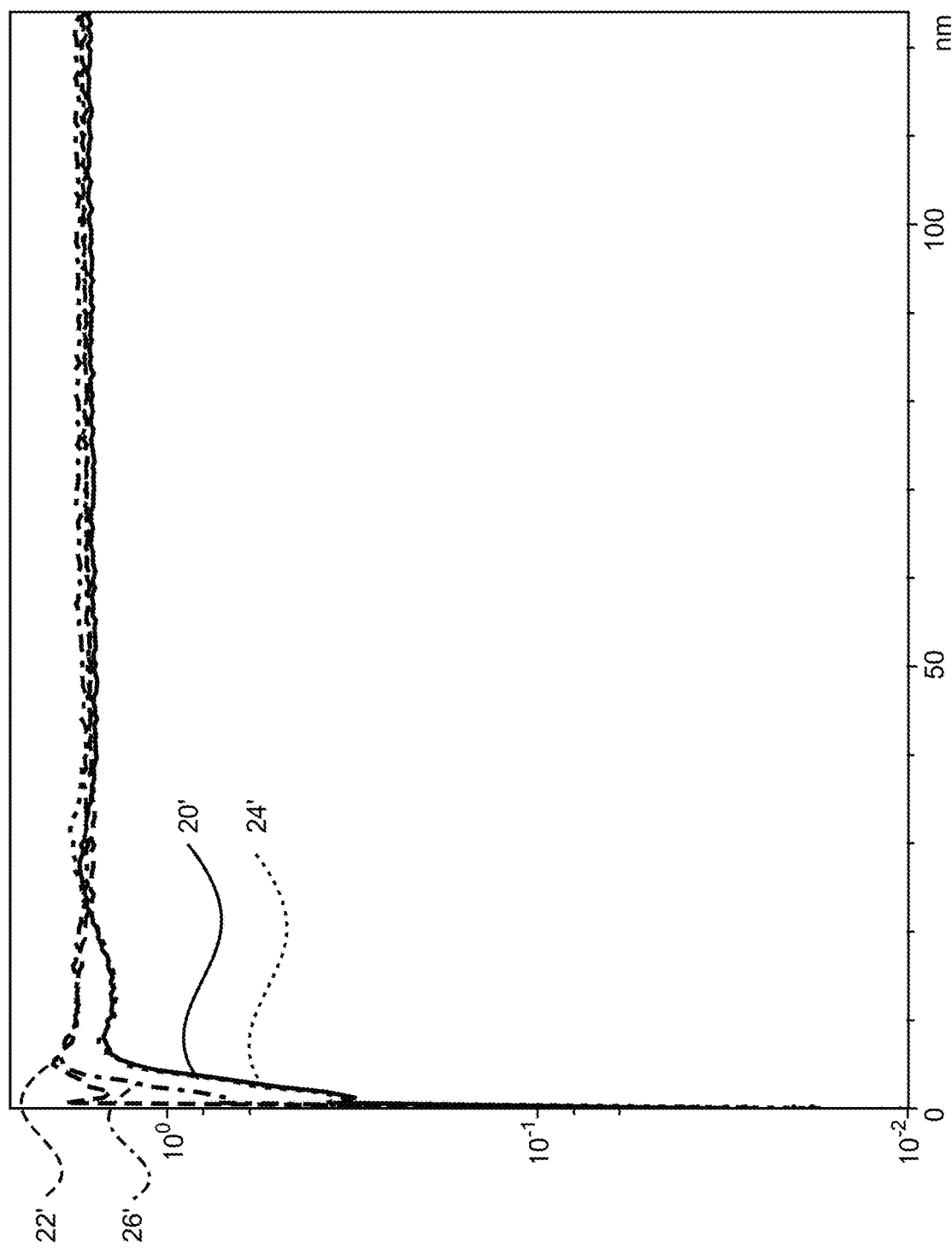

In FIGS. 2a and 2b, the concentration of potassium determined in an analogous way is shown. Once again, four concentration profiles 20, 22, 24 and 26 (and also 20', 22', 24' and 26') were determined as a function of the depth on four different glass reed tubes each having a diameter of 2.06 millimetres.

The potassium concentration profile 20 measured on a first glass tube assumes a minimum value in the region close to the surface. The value increases in the direction of the interior of the glass tube. A maximum value is attained at a distance of about 10 nanometres. Beyond a distance of about 40 nanometres from the surface in the interior of the element, an essentially constant plateau value is attained. The minimum value of the concentration of the potassium is about 0.5 percent of the plateau value or of the maximum value.

The potassium concentration profile 22 measured on a second glass tube displays a somewhat different behaviour. A minimum value is attained at or close to the surface. A maximum value is attained at a depth of about 6 nanometres. Beyond a depth of about 25 nanometres, a plateau value is attained. The minimum value of the concentration of the potassium is about 6 percent of the plateau value or of the maximum value.

The potassium concentration profile 24 measured on a third glass tube displays behaviour similar to the profile 20. A minimum value is attained at or close to the surface. A maximum is attained at a depth of about 10 nanometres. Beyond a depth of about 40 nanometres, an essentially constant plateau value is attained. The minimum value of the concentration of the potassium is about 2 percent of the plateau value or of the maximum value.

A situation analogous to the profile 22 also applies to the concentration profile 26 of the fourth glass. Here, the maximum value is attained at a depth of about 6 nm. Beyond a depth of about 25 nm, a plateau value is attained. The minimum value of the concentration of the potassium is about 2 percent of the plateau value or of the maximum value.

The profiles shown in FIG. 2b correspond essentially to those of FIG. 2a.

Figure 3A:
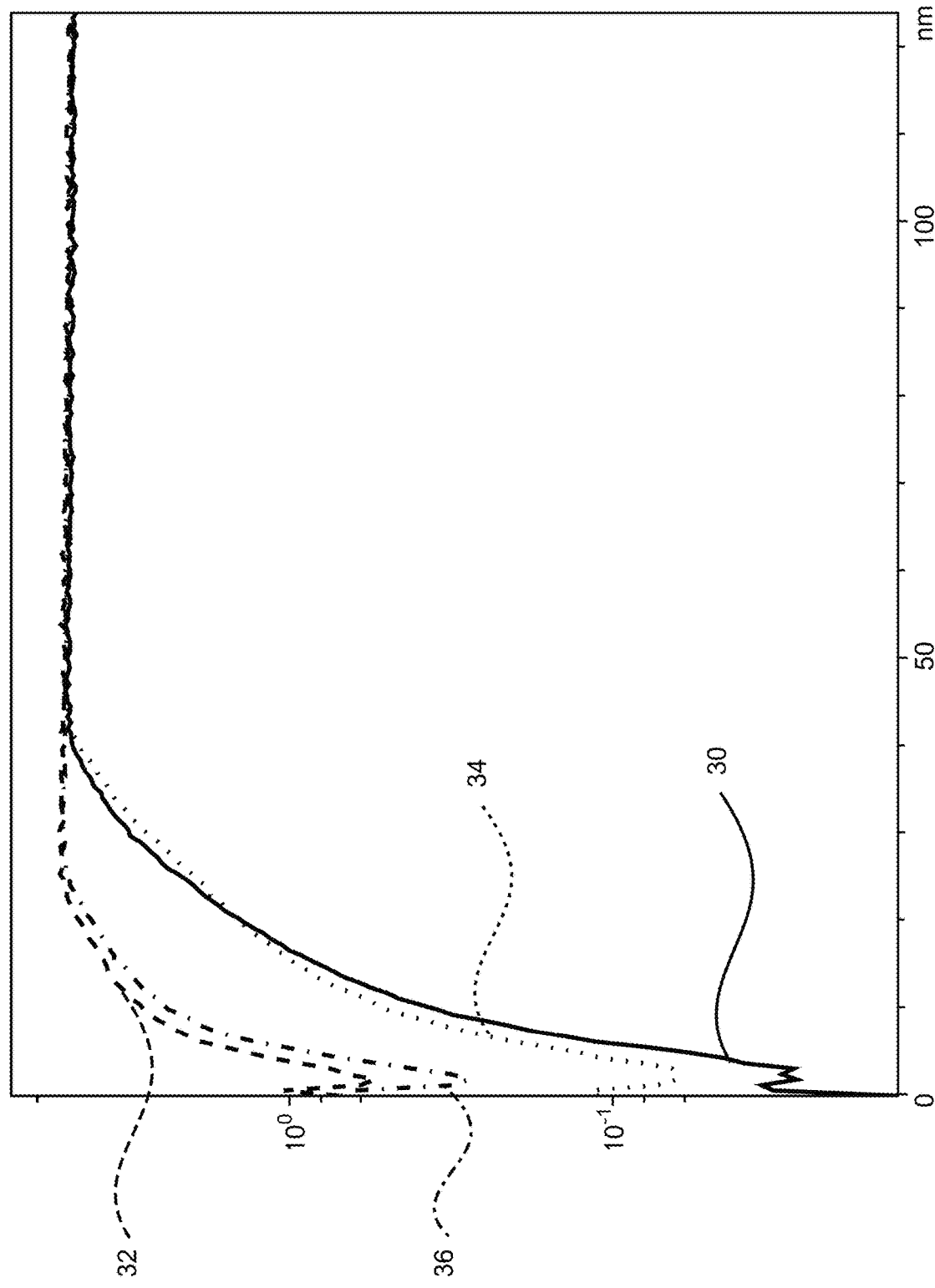

FIGS. 3a and 3b show the concentration of sodium ions determined in an analogous way. Here, the sodium ion concentration is lowest in the region close to the surface for all samples. The concentration profiles 30 and 34 display a plateau value, which represents the maximum value, beyond depths of about 45 nm. In the case of the samples 32 and 36, the plateau value is attained at depths of about 30 nm. Here, the minimum value for the sample 30 is about 0.2% of the plateau value, in the case of the sample 32 is about 11% of the plateau value, in the case of the sample 34 is about 1.3% of the plateau value and in the case of the sample 36 is about 5% of the plateau value.

The profiles shown in FIG. 3b correspond essentially to those of FIG. 3a.

Figure 4A:
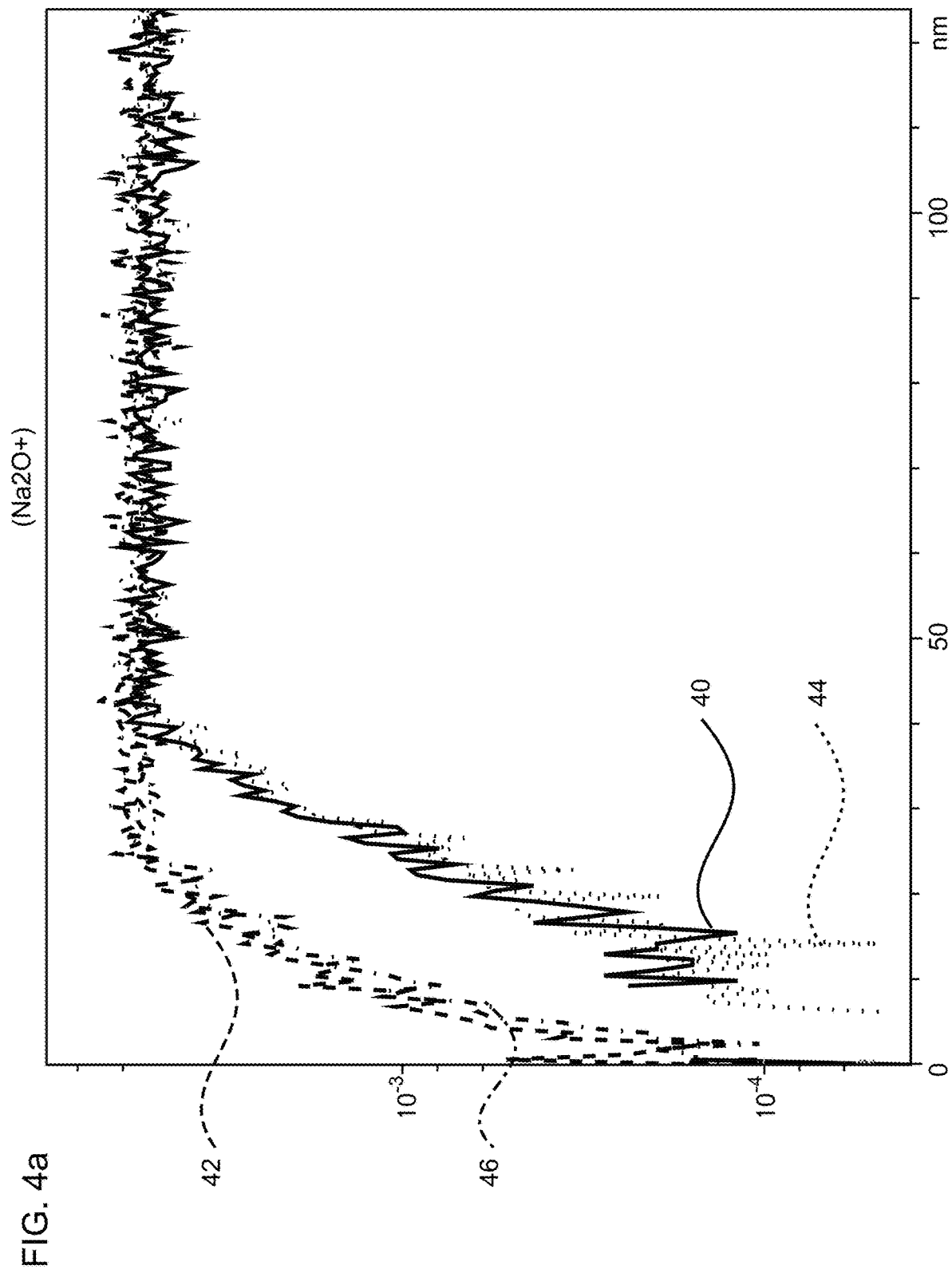

FIGS. 4a and 4b show the concentration of $Na_2O$ determined in an analogous way. Here, the sodium concentration firstly decreases in the region close to the surface for all samples. The concentration profiles 40, 44 display a plateau value, which represents the maximum value, beyond depths of about 40 nm. In the case of the samples 42, 46, the plateau value is attained at depths of about 25 nm.

The profiles shown in FIG. 4b correspond essentially to those of FIG. 4a.

Figure 5A:
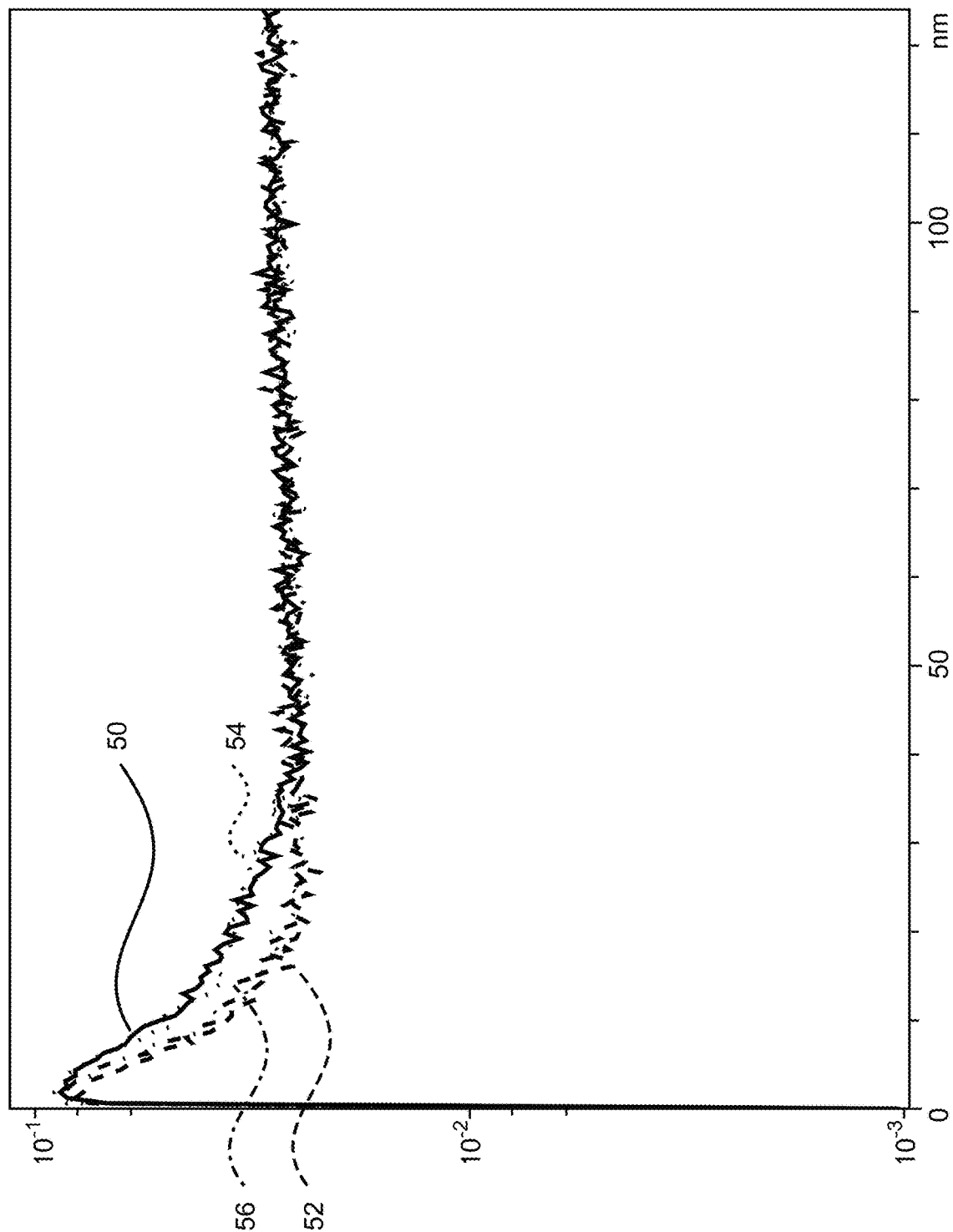
FIGS. 5a and 5b are depth profiles of $Na_2O$ generated by means of ToF-SIMS on four glass reed tubes.
Figure 5B:
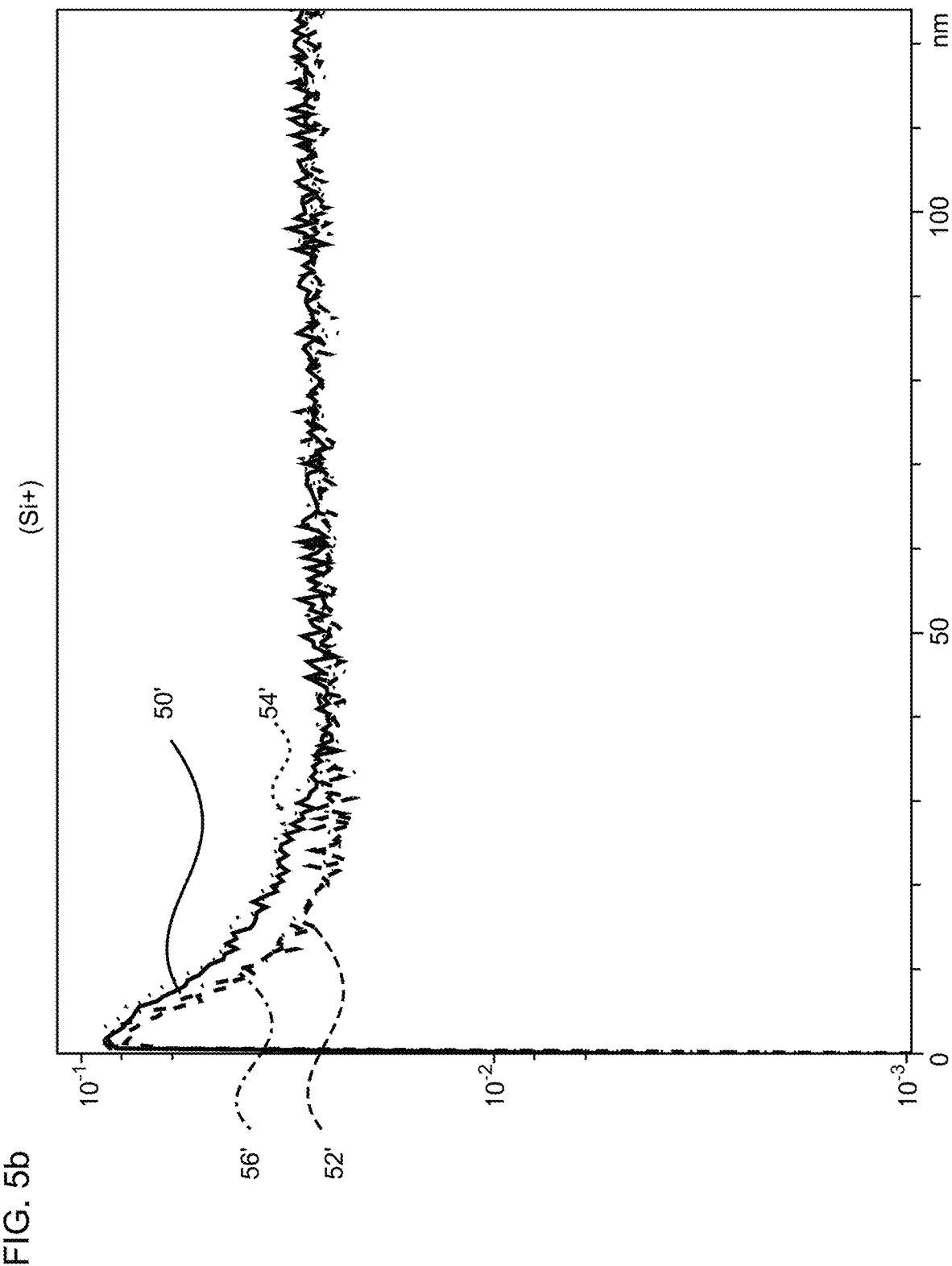

In FIGS. 5a and 5b, the concentration profiles determined for the silicon ions are shown in an analogous way as a function of the glass depth. Here, all samples 50, 52, 54 and 56 have a maximum value in the regions close to the surface of the glass, and this subsequently decreases at about 30 to 40 nm so as to go over into a plateau value which at the same time represents the minimum value.

The profiles shown in FIG. 5b correspond essentially to those of FIG. 5a.

Overall, samples which correspond to the concentration profiles 12, 16, 22, 26, 32, 36, 42, 46, 52, 56 display more advantageous properties for achieving the object of the invention than the samples corresponding to the concentrations profiles 10, 14, 20, 24, 30, 34, 40, 44, 50, 54.

There is also the following relationship to the chemical resistance: glass elements having lower minimum values, in particular of sodium, potassium, lithium, at or close to the surface have an $SiO_2$-rich surface. Such glass elements are therefore more chemically resistant, but can have a higher static charge.

However, the glass elements having relatively high minimum values at or close to the surface surprisingly also have good chemical resistance despite the reduced static charge.

Figure 6:
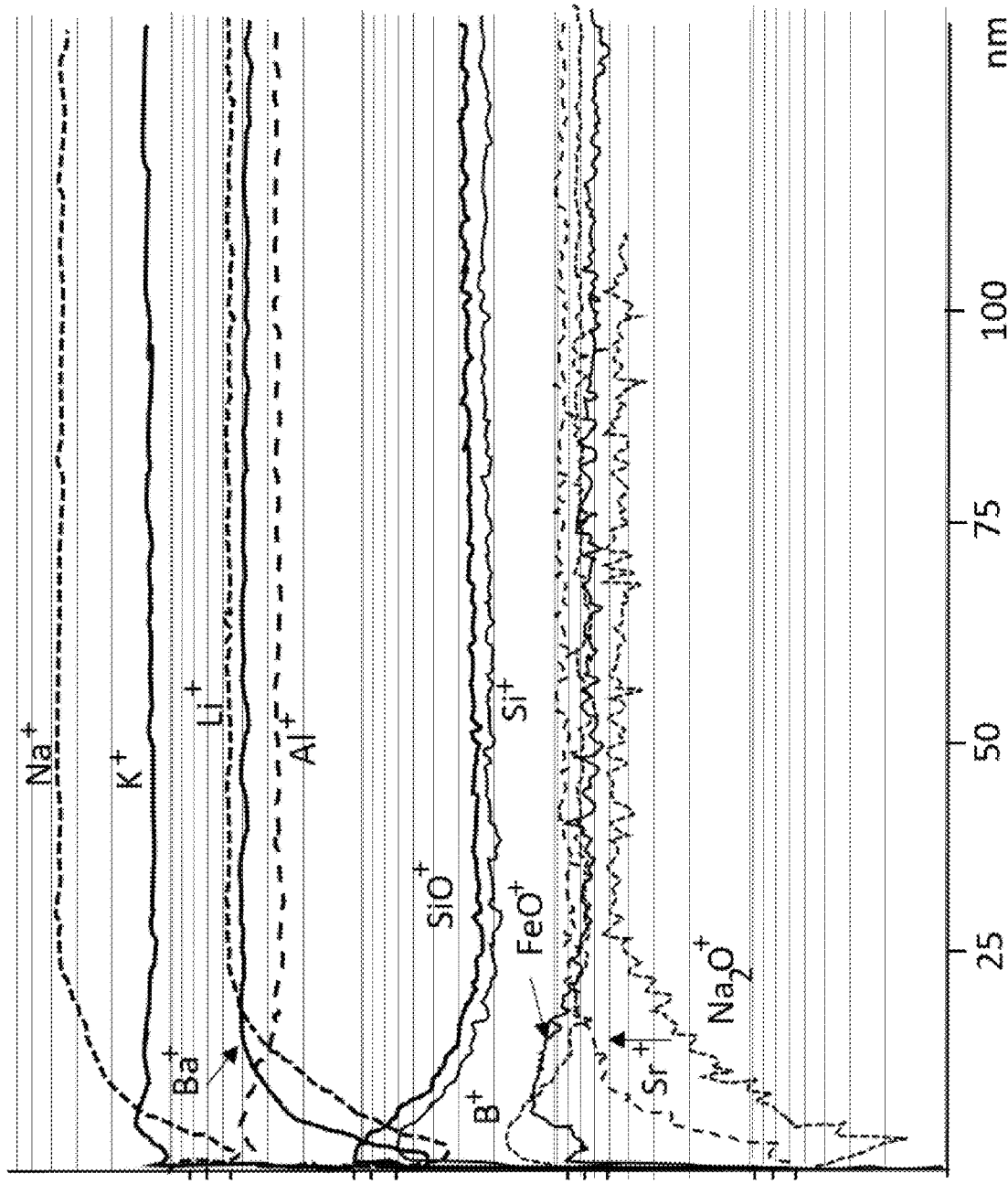
FIG. 6 is depth profiles of various glass components generated by means of ToF-SIMS on a glass reed tube.

FIG. 6 shows the concentration profiles of various ions determined in an analogous way of a sample. This sample, too, in the concentration profiles of the alkali metal ions sodium and lithium shows a reduction in the concentrations in the regions close to the surface with a subsequent concentration increase which goes over into a plateau. The concentration profile of the potassium ions firstly decreases in the regions close to the surface and subsequently assumes a maximum value at a depth of about 10 nm, which subsequently goes over into a plateau at about 20 nm.

In the case of the ions $Si+$, $SiO+$, $B+$ and $Al+$, an increase in the concentrations in the regions close to the surface is firstly observed. With increasing depth, the concentration decreases and goes over into a plateau value which at the same time represents the minimum value.

Figure 7:
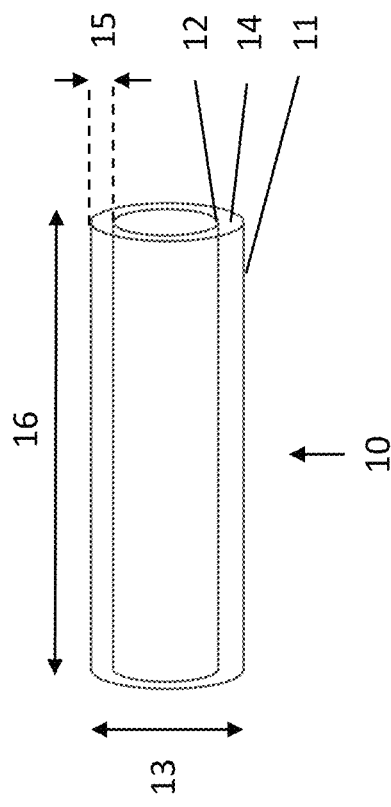
FIG. 7 is a glass tube.

FIG. 7 shows a glass tube 10 formed by a glass element comprising at least one alkali metal and/or an alkali metal oxide. The glass tube 10 has a length 16 and comprises a wall 14 with wall thickness 15. The glass tube 10 and/or the glass wall 14 have an exterior surface 11 as well as an interior surface 12, wherein the concentration of at least one alkali metal and/or the alkali metal oxide increases from one or both of the surfaces in the direction of the interior of the glass element specifically in such a way that the maximum concentration of this alkali metal and/or the alkali metal oxide in the glass element is present at a distance of not more than 60 nanometres measured perpendicularly from the surface or both surfaces.

Figure 9:
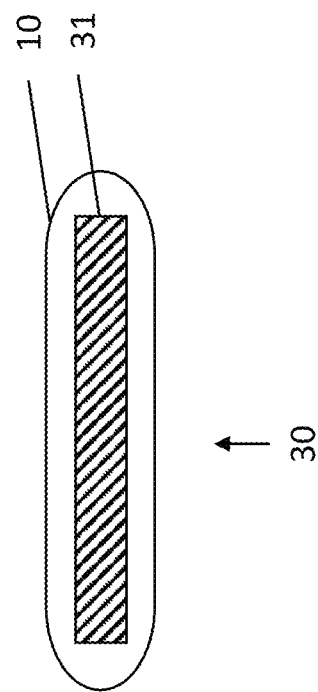
FIG. 9 is a reed switch.
Figure 8:
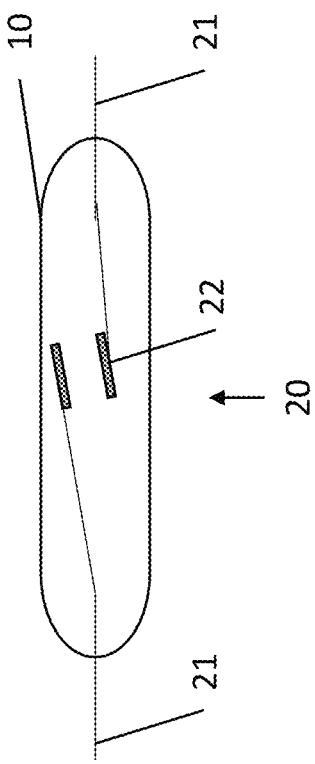
FIG. 8 is a transponder.

FIG. 8 shows a reed switch 20 comprising a closed glass tube 10 forming the glass body of the reed switch 20. The reed switch 20 further comprises two leads 21 which extend through the wall of the glass tube 10. On the inside of the glass tube, the two leads 21 are forming or are connected to switch contacts 22. FIG. 9 shows a transponder 30 comprising a closed glass tube 10 forming the glass body of the transponder 30. In the internal volume of the closed glass tube 10, the transponder 30 further comprises a transponder element 31, such as an RFID element.

What is claimed is:
1. An element comprising:
   glass having a surface and interior, the glass comprising at least one alkali metal and/or an alkali metal oxide,
   wherein the glass comprises, at a distance of at least 50 nanometers measured perpendicularly from the surface, the following proportions in percent by weight on an oxide basis:
   silicon dioxide ($SiO_2$) from 50 to 77 percent,
   aluminum oxide ($Al_2O_3$) from 0 to 10 percent,
   boron trioxide ($B_2O_3$) from 0 to 10 percent,
   iron(III) oxide ($Fe_2O_3$) from 0 to 10 percent,
   sodium oxide ($Na_2O$) from 0 to 18 percent,
   potassium oxide ($K_2O$) from 0 to 17 percent,
   lithium oxide ($Li_2O$) from 0 to 6 percent,
   wherein the glass has a concentration of the at least one alkali metal and/or the alkali metal oxide that increases from the surface in a direction of the interior in such a way that a maximum concentration of the at least one alkali metal and/or an alkali metal oxide is present at a distance of not more than 60 nanometers measured perpendicularly from the surface, and wherein the combined total oxides of Ca, Mg, Ba, Sr and/or Zn is from 1 to 15 percent.

2. The element of claim 1, wherein the concentration of the at least one alkali metal and/or an alkali metal oxide at the surface is at least 2% of the maximum concentration.

3. The element of claim 1, wherein the concentration of the at least one alkali metal and/or an alkali metal oxide at the surface is at least 10% of the maximum concentration.

4. The element of claim 1, wherein the concentration of the at least one alkali metal and/or an alkali metal oxide at the surface is not more than 90% of the maximum concentration.

5. The element of claim 1, wherein the glass comprises at least 0.5% by weight of sodium oxide and the sodium oxide has a concentration that increases from a minimum value at or close to the surface in the direction of the interior,
wherein the sodium oxide concentration reaches constant plateau value in the interior of the glass at a distance of not more than 50 nanometers from the surface, and
wherein the sodium oxide concentration has a minimum value at or close to the surface of at least 1% of the plateau value.

6. The element of claim 5, wherein the sodium oxide concentration has a minimum value at or close to the surface that is not more than 10% of the plateau value.

7. The element of claim 1, wherein the glass comprises at least 0.5% by weight of lithium oxide and the lithium oxide has a concentration that increases from a minimum value at or close to the surface in the direction of the interior, and
wherein the lithium oxide concentration reaches a constant plateau value in the interior of the glass at a distance of not more than 50 nanometers from the surface.

8. The element of claim 7, wherein the lithium oxide concentration has a minimum value at or close to the surface that is at least 1.5% of the plateau value.

9. The element of claim 1, wherein the glass comprises at least 0.5% by weight of potassium oxide and the potassium oxide has a concentration that increases from a minimum value at or close to the surface in the direction of the interior, and
wherein the potassium oxide concentration reaches a constant plateau value in the interior of the glass at a distance of not more than 50 nanometers from the surface.

10. The element of claim 9, wherein the potassium oxide concentration has a minimum value at or close to the surface that is at least 1% of the plateau value.

11. The element of claim 1, wherein the glass comprises $Na_2O$ and $K_2O$, wherein the glass has a ratio of proportions in percent by weight of $Na_2O$ to $K_2O$ that is greater than 0.1.

12. The element of claim 11, wherein the ratio is greater than 1.4.

13. The element of claim 1, wherein the glass further comprises, measured at the distance of at least 50 nanometers measured perpendicularly from the surface, the following proportions in percent by weight on an oxide basis: fluorine (F) from 0 to 4 percent.

14. The element of claim 1, wherein the distance of the maximum concentration of the at least one alkali metal and/or an alkali metal oxide is present at a distance of not more than 20 nanometers measured perpendicularly from the surface.

15. The element of claim 1, further comprising a mean of the maximum concentration and the concentration at the surface that occurs at a distance of at least 1 nanometer and not more than 50 nanometers measured perpendicularly from the surface.

16. The element of claim 1, further comprising a mean of the maximum concentration and the concentration at the surface that occurs at a distance of at least 5 nanometers and not more than 25 nanometers measured perpendicularly from the surface.

17. The element of claim 1, wherein the element is configured as a cylindrical glass tube with an exterior surface, an interior surface, and a uniform wall thickness therebetween.

18. The glass tube of claim 17, wherein the cylindrical glass tube has one or more of: diameter of the exterior surface of less than 6 millimeters, a ratio of the uniform wall thickness to the diameter the exterior surface of less than ⅓, and a ratio of length to the diameter of the exterior surface of less than 50.

19. The element of claim 1, wherein the element is configured as a housing component for an electronic element, a housing for an element that is implantable in the human or animal body.

20. The element of claim 1, wherein the element is configured as a glass tube for reed switches or transponders or implants.

21. An element comprising:
glass having a surface and interior, the glass comprising at least one alkali metal and/or an alkali metal oxide,
wherein the glass comprises, at a distance of at least 50 nanometers measured perpendicularly from the surface, the following proportions in percent by weight on an oxide basis:
silicon dioxide ($SiO_2$) from 50 to 77 percent,
aluminum oxide ($Al_2O_3$) from 0.5 to 7 percent,
boron trioxide ($B_2O_3$) from 0.1 to 8 percent,
iron(III) oxide ($Fe_2O_3$) from 0 to 8 percent,
sodium oxide ($Na_2O$) from 0 to 18 percent,
potassium oxide ($K_2O$) from 0 to 17 percent,
lithium oxide ($Li_2O$) from 0 to 6 percent,
wherein the glass has a concentration of the at least one alkali metal and/or the alkali metal oxide that increases from the surface in a direction of the interior in such a way that a maximum concentration of the at least one alkali metal and/or an alkali metal oxide is present at a distance of not more than 60 nanometers measured perpendicularly from the surface, and
wherein the combined total oxides of Ca, Mg, Ba and Sr is from 0 to 15 percent.

22. An element comprising:
glass having a surface and interior, the glass comprising at least one alkali metal and/or an alkali metal oxide,
wherein the glass comprises, at a distance of at least 50 nanometers measured perpendicularly from the surface, the following proportions in percent by weight on an oxide basis:
silicon dioxide ($SiO_2$) from 50 to 77 percent,
aluminum oxide ($Al_2O_3$) from 0.5 to 7 percent,
boron trioxide ($B_2O_3$) from 0.1 to 8 percent,
iron(III) oxide ($Fe_2O_3$) from 0 to 8 percent,
sodium oxide ($Na_2O$) from 0 to 18 percent,
potassium oxide ($K_2O$) from 0 to 17 percent,
lithium oxide ($Li_2O$) from 0 to 6 percent,
wherein the glass has a concentration of the at least one alkali metal and/or the alkali metal oxide that increases from the surface in a direction of the interior in such a way that a maximum concentration of the at least one alkali metal and/or an alkali metal oxide is present at a distance of not more than 60 nanometers measured perpendicularly from the surface, and wherein the combined total oxides of Ca, Mg, Ba, Sr and Zn is from 3.5 to 17 percent.

* * * * *